(12) United States Patent
Tai

(10) Patent No.: US 9,492,644 B2
(45) Date of Patent: Nov. 15, 2016

(54) DILATION DEVICE FOR PLACING CATHETER TUBES

(71) Applicant: AVENT, INC., Alpharetta, GA (US)

(72) Inventor: Kok-Ming Tai, Lawrenceville, GA (US)

(73) Assignee: Avent, Inc., Alpharetta, GA (US)

( * ) Notice: Subject to any disclaimer, the term of this patent is extended or adjusted under 35 U.S.C. 154(b) by 782 days.

(21) Appl. No.: 13/723,932

(22) Filed: Dec. 21, 2012

(65) Prior Publication Data

US 2014/0180242 A1 Jun. 26, 2014

(51) Int. Cl.
*A61M 31/00* (2006.01)
*A61M 29/02* (2006.01)
*A61J 15/00* (2006.01)
*A61M 25/10* (2013.01)

(52) U.S. Cl.
CPC .......... *A61M 29/02* (2013.01); *A61J 15/0015* (2013.01); *A61M 2025/1072* (2013.01)

(58) Field of Classification Search
CPC ................ A61M 29/02; A61M 2025/0172; A61J 15/00; A61J 15/0015
USPC ............ 600/424; 604/96.01, 101.01, 101.05, 604/103.05, 103.07, 103.09, 506, 509; 606/198
See application file for complete search history.

(56) References Cited

U.S. PATENT DOCUMENTS

| | | | |
|---|---|---|---|
| 5,458,583 A | 10/1995 | McNeely et al. | |
| 6,019,746 A | 2/2000 | Picha et al. | |
| 6,236,879 B1 | 5/2001 | Konings | |
| 7,273,056 B2 | 9/2007 | Wilson et al. | |
| 7,396,354 B2 | 7/2008 | Rychnovsky et al. | |
| 7,757,695 B2 | 7/2010 | Wilson et al. | |
| 2001/0053920 A1* | 12/2001 | Shaker | A61B 5/037 606/197 |
| 2003/0055470 A1* | 3/2003 | Mon | A61B 18/1815 607/101 |
| 2003/0100909 A1 | 5/2003 | Suzuki | |
| 2003/0225312 A1 | 12/2003 | Suzuki et al. | |
| 2006/0095066 A1 | 5/2006 | Chang et al. | |
| 2007/0149898 A1* | 6/2007 | Inderbitzen | A61M 25/09 600/585 |

(Continued)

FOREIGN PATENT DOCUMENTS

| WO | WO 02/19890 A2 | 3/2002 |
|---|---|---|
| WO | WO 2008/154533 A1 | 12/2008 |
| WO | WO 2011/159590 A2 | 12/2011 |

OTHER PUBLICATIONS

Co-pending U.S. Appl. No. 13/245,562, filed Sep. 26, 2011, by Tai et al. for "Multi-Balloon Dilation Device for Placing Catheter Tubes."

(Continued)

*Primary Examiner* — Theodore Stigell
*Assistant Examiner* — Tiffany Legette
(74) *Attorney, Agent, or Firm* — Dority & Manning, P.A.

(57) ABSTRACT

A stoma dilation device that includes a tubular support and an inflatable dilation portion located on the tubular support. The inflatable dilation portion includes a stiffening portion and inflation lumen. The device may have a retention portion configured to have a diameter upon full, unrestrained inflation that is greater than the diameter of the dilation portion. The device is designed to be placed in a patient to dilate the stoma for the installation of a catheter feeding tube. The device may be placed and withdrawn with the use of an endoscope which need be inserted into the patient only one time. The single insertion of the endoscope significantly reduces the trauma to the patient in comparison with multiple endoscope insertion methods.

8 Claims, 7 Drawing Sheets

(56) References Cited

U.S. PATENT DOCUMENTS

| | | |
|---|---|---|
| 2007/0225677 A1* | 9/2007 | Rowe et al. .................. 604/509 |
| 2008/0194973 A1 | 8/2008 | Imam |
| 2008/0228066 A1 | 9/2008 | Waitzman |
| 2008/0287983 A1 | 11/2008 | Smith et al. |
| 2009/0281379 A1 | 11/2009 | Binmoeller et al. |
| 2009/0318757 A1 | 12/2009 | Singh |
| 2009/0318798 A1 | 12/2009 | Singh et al. |
| 2010/0087706 A1 | 4/2010 | Syed et al. |
| 2010/0198005 A1 | 8/2010 | Fox |
| 2011/0125132 A1* | 5/2011 | Krolik .............. A61B 17/22032 604/509 |

OTHER PUBLICATIONS

Co-pending U.S. Appl. No. 13/245,577, filed Sep. 26, 2011, by Tai et al. for "Dilation Device for Placing Catheter Tubes."

* cited by examiner

DILATION DEVICE FOR PLACING CATHETER TUBES

This application claims the benefit of U.S. patent application Ser. No. 13/600,827 filed Aug. 31, 2012.

BACKGROUND

This disclosure relates to catheters such as feeding tubes and their placement in the body of a patient.

Numerous situations exist in which a body cavity or lumen needs to be catheterized through an artificial opening or stoma to achieve a desired medical goal. One relatively common situation is to provide nutritional solutions or medicines directly into the stomach or intestines. A stoma is formed in the stomach or intestinal wall and a catheter is placed through the stoma. This surgical opening and/or the procedure to create the opening is commonly referred to as "gastrostomy". Feeding solutions can be injected through the catheter to provide nutrients directly to the stomach or intestines (known as enteral feeding). A variety of different catheters intended for enteral feeding have been developed over the years, including some having a "low profile" relative to the part of the catheter which sits on a patient's skin, as well as those having the more traditional or non-low profile configuration. These percutaneous transconduit catheters (sometimes referred to as "percutaneous transconduit tubes") are frequently referred to as "gastrostomy catheters", "percutaneous gastrostomy catheters", "PEG catheters", PEG tubes or "enteral feeding catheters". U.S. Pat. No. 6,019,746 for a "Low Profile Balloon Feeding Device" issued to Picha et al. on Feb. 1, 2000, provides an example of one device.

PEG catheters or tubes are frequently placed in a procedure called percutaneous endoscopic gastrostomy (frequently referred to as PEG). Traditionally, a PEG tube is placed using endoscopic guidance or x-ray guidance. In a conventional PEG procedure that places a PEG tube into a patient's stomach, an endoscope is used to observe that the patient's esophagus is unobstructed and to inspect and inflate the stomach to see that the area selected for the gastrostomy can be distended. If the location is suitable, this spot is selected.

Insufflation of the gastric lumen has been found to be successful in maintaining the lumen in close proximity of the abdominal wall in some procedures. This procedure is also applicable to jejunostomy or gastro-jejunostomy as well as the gastrostomy procedure referred to above. Similar procedures may also be applicable or desirable for other catheter tubes such as peritoneal drainage tubes.

A needle is inserted into the patient in the area in the appropriate location. Additionally, a small incision may be made in the skin. An endoscopist will then typically watch through the endoscope as a needle pushes through the patient's skin, then through the abdominal wall, and enters the gastric lumen in the selected area to form a needle tract. A guide wire is passed through the needle into the gastric lumen (e.g., the stomach). The endoscopist will use an endoscopic snare to grasp the guide wire firmly. The snare, passed through the working channel of the endoscope, firmly grabs the guide wire. Both the endoscope and snare are then withdrawn together through the patient's mouth, pulling the guide wire with them. The end of the guide wire that extends out from the patient's mouth is subsequently attached to a PEG tube and the other end of the guide wire remains outside the patient's skin in the abdominal region.

The PEG tube is guided into the patient's mouth (while the endoscope is completely removed from the patient) and pulled into the patient's gastric lumen as the guide wire is pulled from the end that remains outside the patient's skin. Once the PEG tube is in the gastric lumen, it is pulled partially through the gastric and abdominal walls until a bumper of the PEG tube is snug against the gastric mucosa. However, in order for the PEG tube to be pulled partially through the gastric and abdominal walls and skin, the original needle tract must be dilated. This dilation is carried out with conventional dilation devices that employ a tapered dilator at the distal end of the PEG tube so that it dilates the opening as it is pulled through the gastric mucosa. During such dilation, the endoscope is again passed into the patient and subsequently used to visually observe that the bumper of the PEG tube is snug against the gastric mucosa.

In other conventional PEG tube placement procedures, endoscopy is not used at all. Instead, x-ray techniques are used to help select a particularly suitable location in the patient's body (e.g., the stomach) for the introduction of the PEG tube. X-ray is used for guiding the PEG tube placement and for inspecting the PEG tube's final position.

There are problems associated with these conventional procedures, notably an increased risk of esophageal trauma associated with multiple passes of an endoscope and components into and out of a patient or placement of the PEG tube in an improper location. It would be desirable to avoid the complications and reduce the steps of such procedures. While avoiding these complications may be desirable, suitable devices or procedures are lacking.

Because PEG tubes tend to have flexible in-dwelling sections, they can present insertion problems into the stoma from outside the patient's body, e.g. they can bend, kink or distort.

Accordingly, there is a need for a device, system and method for placing a non-vascular catheter tube such as a PEG tube in a patient that reduces these risks and trauma and is easy to perform.

SUMMARY

In response to the difficulties and problems discussed herein, this disclosure describes a dilation device and dilation system. The dilation device has at least one inflatable component and the device is used for placing catheter tubes in a non-vascular lumen, desirably under direct visualization using an endoscope. The device may be placed by the use of an endoscope that need be inserted into the patient only a single time. In addition, the dilation device and the feeding tube may use the same incision, allowing for the entire procedure to occur using a single incision.

The dilation device includes an inflatable stiffening portion and an inflatable dilation portion. The device also includes at least one inflation lumen to inflate and deflate any inflatable components. The device may optionally have a continuous pathway through the device that accommodates a guide wire. The device optionally has a retention portion that is adjacent an end of the dilation portion. When present, the retention portion may be a portion of the at least one inflatable balloon or it may be an additional balloon. When the device has the retention portion, it desirably has a flexible section between the dilation portion and retention portion that allows a degree of movement between the dilation portion and retention portion.

The device may also be made such that the above portions are sections of a single balloon or they are separate balloons that may be inflated separately. When the portions are separate balloons, separate inflation lumens are required for each balloon. Balloons of the device may be compliant, semi-compliant, non-compliant, or of combined compliances.

With respect to the device, the stiffening portion is towards the proximal end, the retention portion is towards the distal end, and the dilation portion is immediately next to the stiffening portion.

According to this disclosure, a conventional endoscope is advanced into a gastric lumen to insufflate and allow palpation to locate an appropriate site. Once the appropriate site is located, a needle is inserted into the gastric lumen through the abdomen from outside the body to form a needle tract. A guide wire is then introduced into the gastric lumen through the needle and is caught by the endoscope. The dilation device is passed through the endoscope and pulled at least partially through the needle tract where it is used to dilate the tract to create a stoma. The stiffening portion of the device is sized to fit within a lumen opening of a distal end of an enteral feeding catheter tube in order to facilitate placement (insertion) of the catheter, e.g. PEG tube, into the stoma. The feeding tube may be placed by the "push" or "pull" method.

The stiffening portion has a length and diameter upon inflation to fit within various catheter tubes. The dilation portion may be dilated to various effective diameters using respectively different inflation pressures. The retention portion may be designed to have substantially the same inflated diameter features of the inflated dilation portion or it may have a section with an inflated larger diameter than any diameters of the inflated dilation portion. The device has the inflatable portions assembled together to form two opposing ends. At least one end is attached to a tubular support. It is contemplated that any inflation lumens included in the dilation device can serve as the tubular support. The dilation device may optionally have a continuous single pathway through its entirety to accommodate a guide wire. Alternatively the dilation device may have a continuous single pathway from one of the opposing ends and this pathway may include an inflation lumen. A better understanding of the above and many other features and advantages of the dilation device may be obtained from a consideration of the detailed description of this disclosure below, particularly if such consideration is made in conjunction with the appended drawings.

DETAILED DESCRIPTION

Reference will now be made to the drawings in which the various elements of the present disclosure will be given numeral designations and in which the disclosure will be discussed so as to enable one skilled in the art to make and use the disclosure. It is to be understood that the following description is only exemplary of the principles of the present disclosure, and should not be viewed as narrowing the pending claims. Those skilled in the art will appreciate that aspects of the various embodiments discussed may be interchanged and modified without departing from the scope and spirit of the disclosure.

Since the stomach is a common example of a non-vascular lumen, for the purpose of describing this disclosure, the use of the term "gastric lumen" or "stomach" is representative of all other non-vascular lumens or spaces (e.g., duodenum, jejunum, ileum, peritoneal cavity, etc.), unless otherwise specified.

Figure 1:
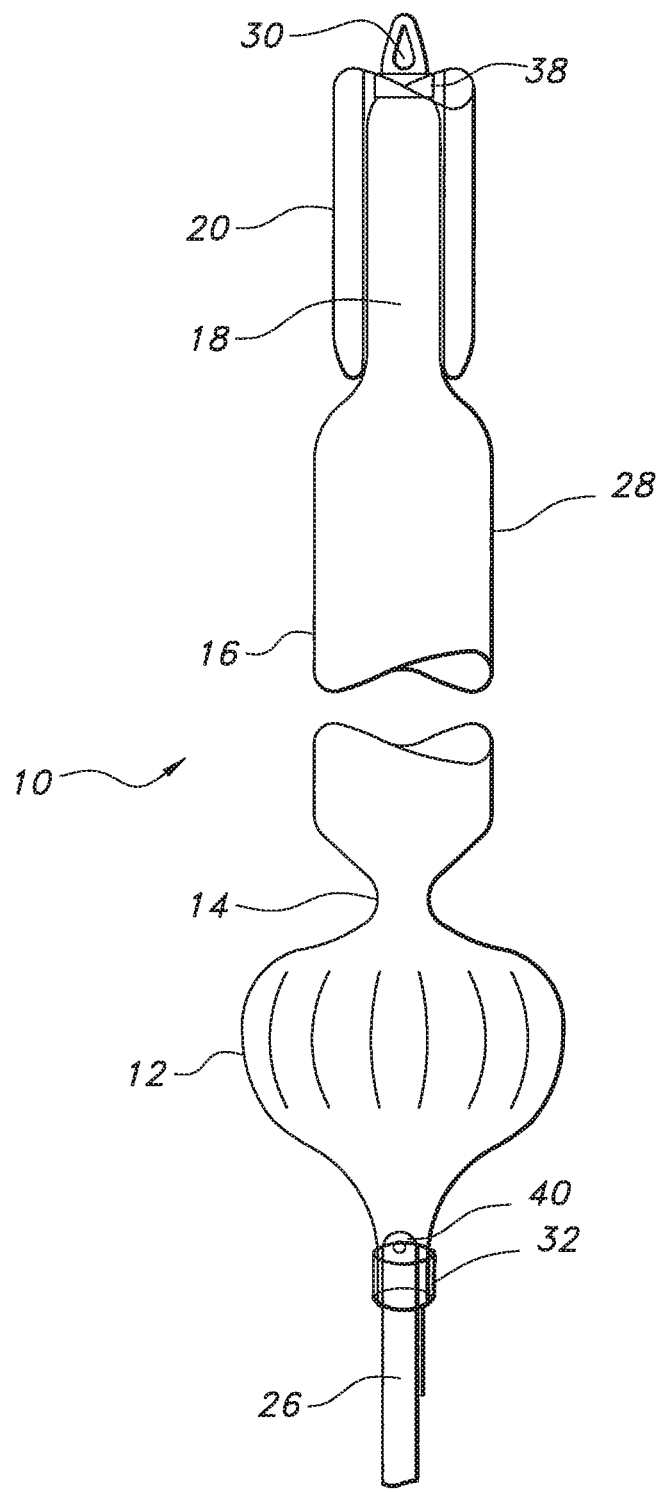
FIG. 1 is an exemplary dilation device that has a tubular support on the distal end upon which is mounted an inflatable balloon having a stiffening portion, a dilation portion, a flexible portion and a retention portion. The stiffening portion is shown within a lumen opening of a feeding catheter tube.

Turning now to the drawings, there is shown at FIG. 1 an exemplary dilation device 10. The device 10 includes a balloon 28 having a stiffening portion 18, a dilation portion 16 and optionally a retention portion 12. There is desirably a flexible section 14 between the retention portion 12 and the dilation portion 16. The flexible section 14 allows some degree of movement or flexing of the balloon 28 between the retention portion 12 and the dilation portion 16. In this embodiment the balloon 28 is mounted on its distal end to a tubular support 26 at a collar 32 and at its proximal end to the tubular support at a collar 38. The stiffening portion 18 inserts into the enteral feeding catheter tube 20 to help insertion of the tube 20 into the stoma, as will be discussed in greater detail below.

The embodiment of FIG. 1 is for the dilation device 10 that contains only one balloon 28. The balloon 28 is inflated by gradually introducing controlled amounts of fluid (e.g., liquid or gas) to increase pressure in balloon 28. The dilation portion 16 of the balloon 28 is placed in the needle tract and inflates, generally in a radial manner, to provide relative atraumatic dilation (as compared to serial dilation) of the entire needle tract to create the desired stoma. The retention portion 12 of the device 10 inflates inside the stomach and not in the needle tract. The retention portion 12 is used to stabilize the device 10 and to help prevent the device from pulling out of the stoma tract during the procedure. The stiffening portion 18 of the device 10 inflates inside a feeding tube 20 so that it imparts rigidity along the insertion length of tube 20 and facilitates advancement of tube 20 into the stoma.

The dilation device 10 of the Figures has at least one inflation lumen 40 to inflate and deflate the portions. Desirably, the inflation lumen is integrated in the tubular support 26. In this regard, the tubular support 26 may define multiple lumens to inflate and deflate the portions. It is contemplated that the inflation lumens may be separated from the tubular support 26 and be in the form of pilot tubes or the like. The tubular support 26 is desirably flexible so that trauma or damage to the stomach may be minimized during the procedure. The tubular support 26 may be made in sections for flexibility or may be made from a flexible polymer. The device 10 may also have a pull loop 30 to allow the device to be pulled into the stoma, e.g. via an attached guide wire.

Figure 2:
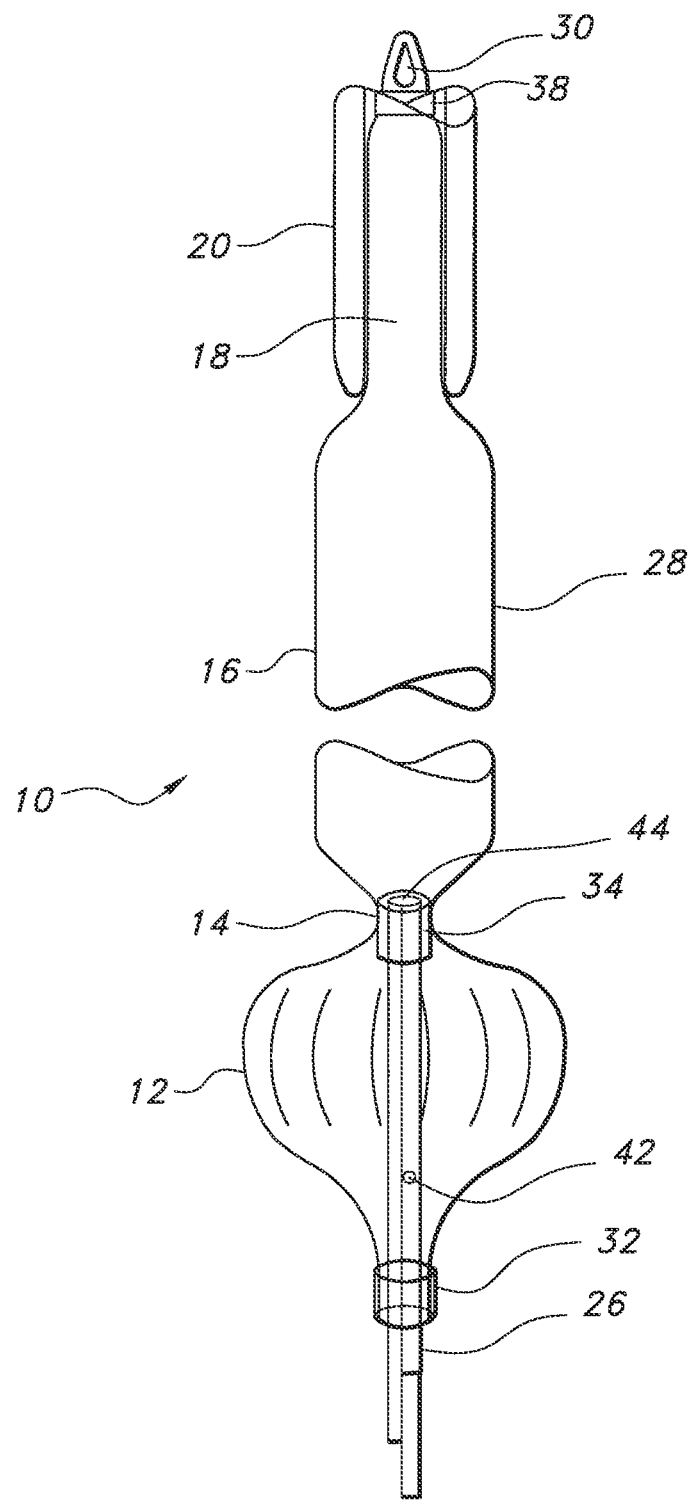
FIG. 2 is another exemplary dilation device showing an inflatable balloon having a stiffening portion and a dilation portion that may be inflated together and a retention portion that may be inflated separately.

FIG. 2 is an illustration of an embodiment of the device 10 where the stiffening 18 and dilation 16 portions are inflated together and the retention portion 12 is inflated separately from the stiffening and dilation portions 16, 18. The tubular support 26 extends through the retention portion 12 and is attached to distal and proximal ends of the retention portion 12 at collars 32, 34 and at the proximal end of the stiffening portion at a collar 38. The stiffening, dilation and retention portions 18, 16, 12 may all be parts of a single balloon that is inflated in two sections where the retention portion 12 is fluidly separated from the two other portions by the collar 34. Alternatively, the stiffening and dilation portions 18, 16 may be one balloon and the retention portion 12 may comprise a separate balloon, again fluidly separated by the collar 34. As is illustrated, inflation lumen 42 is in fluid communication with the retention portion 12 and inflation lumen 44 is in fluid communication with the stiffening and dilation portions 16, 18. The portions of the dilation device 10 inflate by gradually introducing controlled amounts of fluid (e.g., liquid or gas) to increase pressure within the portions via inflation lumens 42 and 44. Inflation lumen 44 is used to inflate the dilation portion 16 to provide relative atraumatic dilation of the entire needle tract to create the desired stoma tract. The retention portion 12 of the device 10 may be inflated if needed or may be left deflated as desired by the medical personnel. The stiffening portion 18 of the device 10 inflates inside a feeding tube 20 so that it imparts temporary rigidity along the insertion length of tube 20 and facilitates advancement of tube 20 into the stoma.

Figure 3:
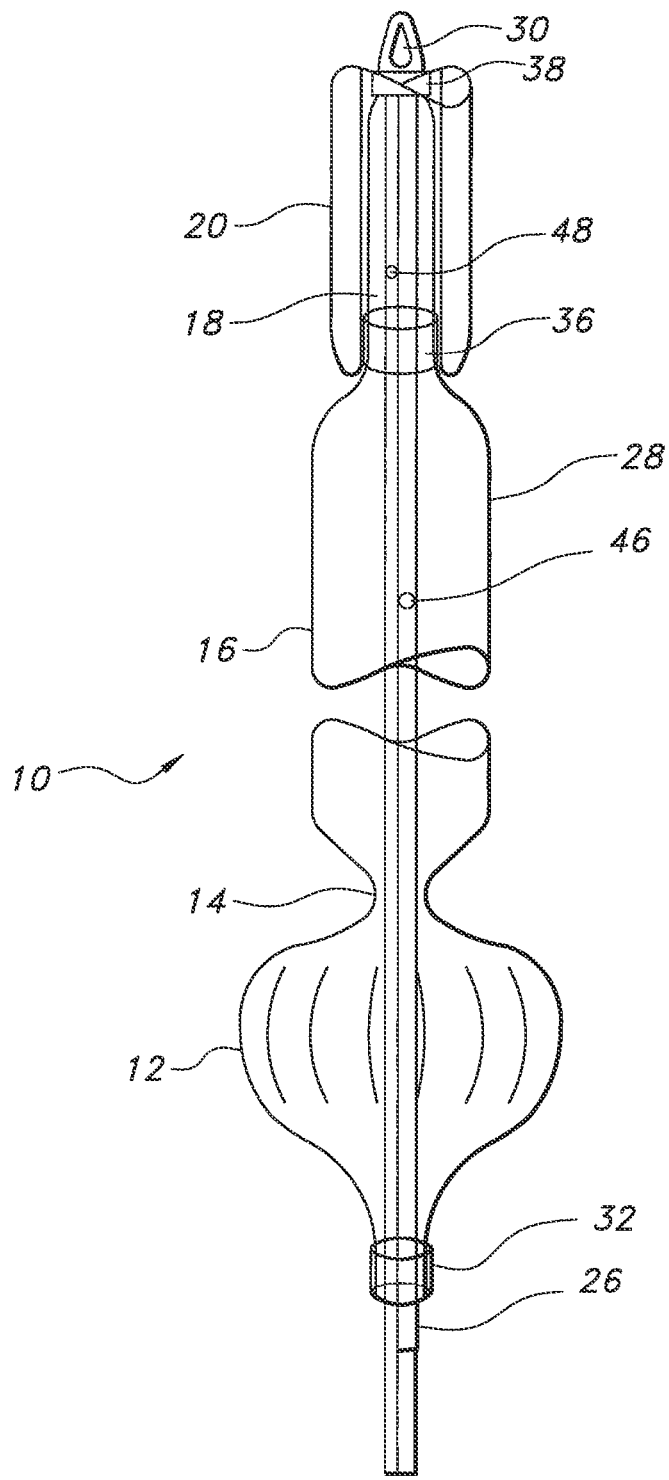
FIG. 3 is another exemplary dilation device showing an inflatable balloon having a stiffening portion that may be inflated separately and a dilation portion and a retention portion that may be inflated together.

FIG. 3 is an illustration of an embodiment of the device 10 where the dilation portion 16 and retention portion 12 are inflated together and the stiffening portion 18 is inflated separately from the dilation and retention portions 16, 12. The tubular support 26 extends through the entire device and attaches to the distal end of the retention portion 12 at a collar 32 and to the distal and proximal ends of the stiffening portion 18 at collars 36, 38. The stiffening, dilation and retention portions 18, 16, 12 may all be parts of a single balloon that is inflated in two sections where the stiffening portion 18 is fluidly separated from the two other portions by the collar 36. Alternatively, the dilation and retention portions 16, 12 may be one balloon and the stiffening portion 18 may comprise a separate balloon, again fluidly separated by the collar 36. As is illustrated, the inflation lumen 46 is in fluid communication with the retention and dilation portions 12, 16 and the inflation lumen 48 is in fluid communication with the stiffening portion 18.

Like the previous embodiments, the inflatable portions inflate by gradually introducing controlled amounts of fluid (e.g., liquid or gas) to increase pressure within the respective portions; the dilation portion 16 inflates to provide relative atraumatic dilation (as compared to serial dilation) of the entire needle tract to enlarge the stoma tract; the proximal retention portion 12 of the device 10 inflates inside the stomach (and not in the needle tract) where it is used to stabilize the device 10 and to help prevent the device from pulling out of the stoma tract during the procedure; the stiffening portion 18 inflates separately. As desired, the stiffening portion 18 inflates inside the feeding tube 20 so that it imparts rigidity along the insertion length of the tube 20 and facilitates advancement of the tube 20 into the stoma.

Figure 4:
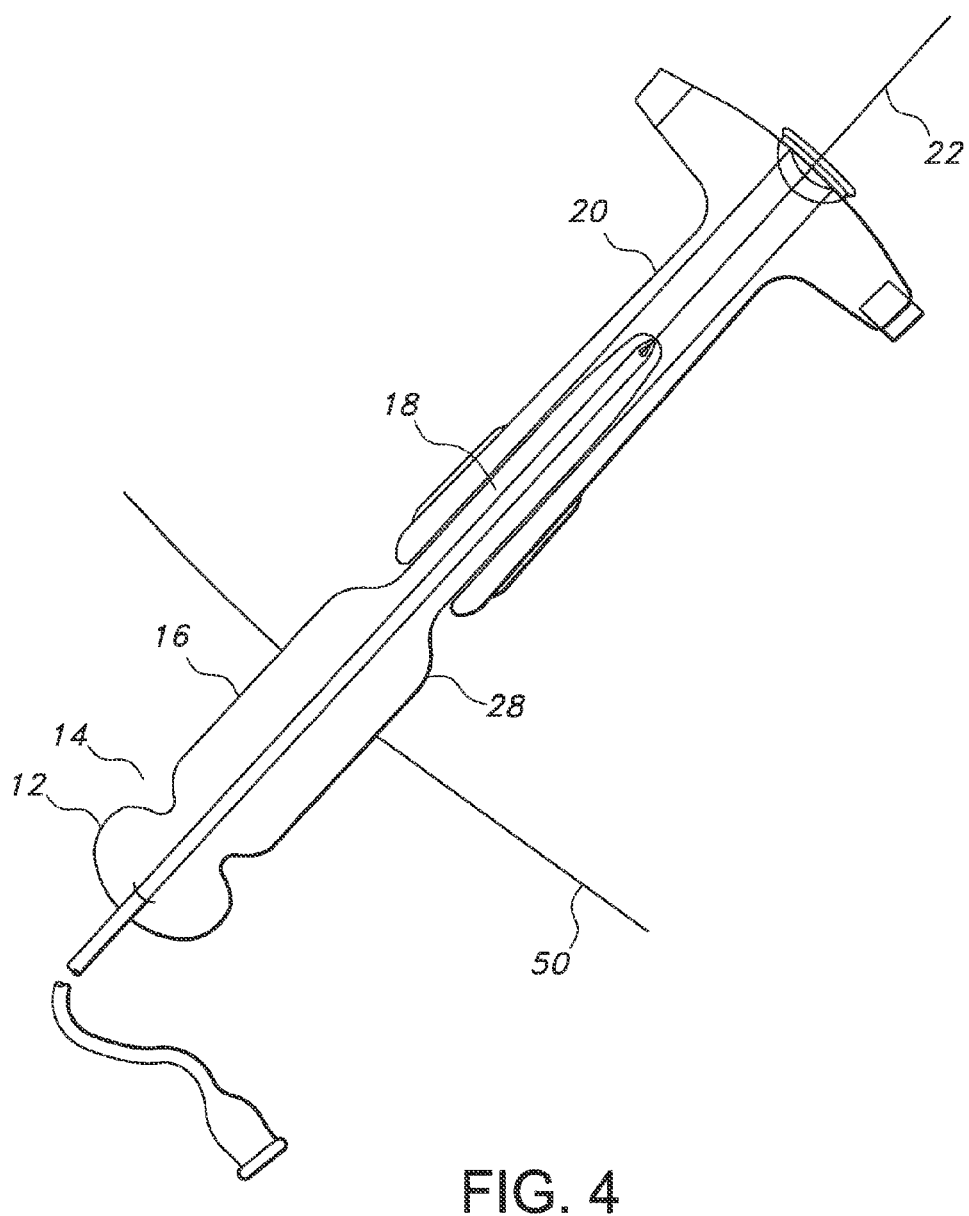
FIG. 4 shows a device embodiment with the dilation, stiffening, and retention portions as a single balloon. The device is shown in position to be inflated in a stoma with the stiffening portion inserted into a catheter feeding tube. The dilation portion is located partially on the exterior of the patient.

FIG. 4 shows a single balloon embodiment and the device 10 in position to be inflated in a stoma with the stiffening portion 18 inserted into the distal end of a catheter feeding tube 20. The dilation portion 16 is located in the stoma and partially on the exterior 50 of the patient. The balloon 28 inflates by gradually introducing controlled amounts of fluid (e.g., liquid or gas) to increase pressure in the balloon so the dilation portion 16 smoothly and gradually expands the needle tract into a stoma tract. The retention portion 12 of the dilation balloon 28 also inflates as the dilation portion 16 inflates. When the retention portion 12 becomes larger than the dilation portion 16 and expands to full inflation, it stabilizes the stomach wall by bringing it up against the wall of the abdomen. At the same time, the stiffening portion 18, which had been inserted into the end of a catheter feeding tube 20, expands to touch and eventually hold by friction and compression the tube 20.

The retention portion has a substantially larger cross-section or diameter upon full, unrestrained inflation than any diameters of the dilation portion 16 as is generally illustrated in FIGS. 1, 2 and 3. Generally speaking, the retention portion 12 may have a cross-section or diameter that is about 1.5 times to about 3 times the diameter of the dilation portion 16. Once this retention portion 12 is inflated, it functions to stabilize the wall of the lumen and/or provide retention of the dilation device within the non-vascular lumen (e.g., the stomach).

The retention portion 12 may have a circular or non-circular cross-section as long as it is able to function as described above. The retention portion 12 may have or lack a cross-section with one axis of symmetry. The retention portion 12 may, for example, have a square, rectangular, triangular, elliptical, oval or other geometric shape. Alternatively and/or additionally the retention portion 12 may incorporate lobes, fingers or projections that contribute to a cross-sectional dimension that is greater than the diameter of the dilation portion 16.

The dilation portion 16 of the balloon has a length and a general circular cross-section with a pre-determined diameter along the length that, upon full inflation, produces a stoma that allows for the insertion of the desired size catheter feeding tube. Alternatively, the dilation portion 16 may be dilated to various effective diameters using respectively different inflation pressures to fit various outer diameters of catheter tubes. As one example, the effective inflated diameter of the dilation portion 16 may range from about 3 to about 10 millimeters. As another example, the effective inflated diameter of the dilation portion 16 may range from about 2 to about 8 millimeters. An inflated dilation portion with a length and with a non-circular cross-section along the length, e.g. elliptical or oval, is also contemplated.

The stiffening (or gripping) portion 18 functions to grip and/or stiffen catheter tube 20 when catheter tube 20 fits over the stiffening portion 18 and the stiffening portion 18 is appropriately inflated to contact, e.g. compress against, the inside of the lumen of an enteral feeding tube 20. As shown in FIGS. 1, 2 and 3, the stiffening portion 18 inserts into the tube 20 after the balloon 28 is in place in the non-vascular lumen and stoma. The stiffening portion 18, once inflated, creates a strong temporary connection with the inside surface of the tube 20 via friction and some degree of compression. This temporary connection allows the tube 20 to be pushed into the stomach by the medical professional, usually by hand. This temporary connection alternatively also allows the tube 20 to be pulled into the stomach by the medical professional by pulling the device into the stomach, e.g. via a connection that passes through the endoscope.

Figure 6:
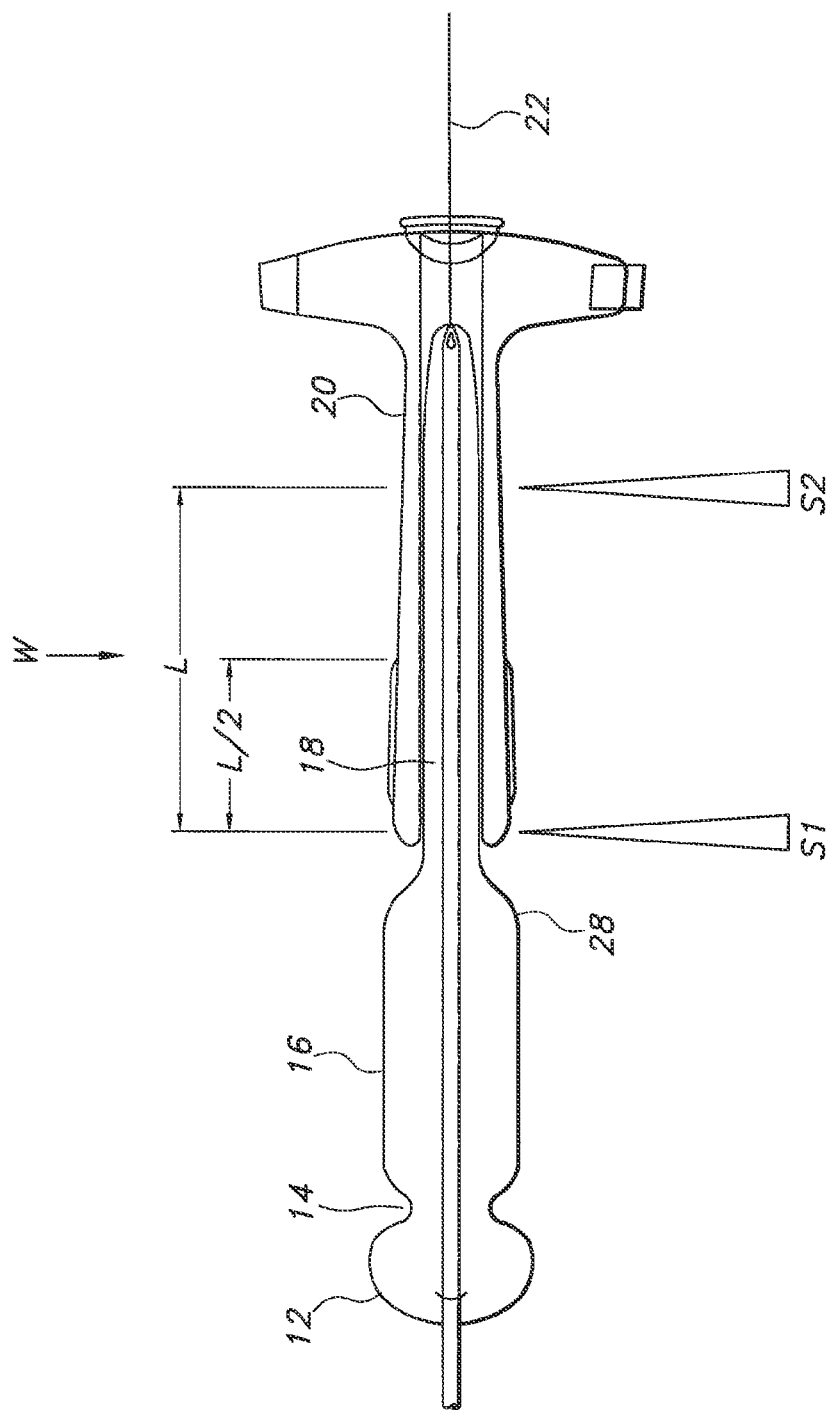
FIG. 6 shows a device with the stiffening portion inserted into a feeding tube and showing a test set-up for measuring the stiffness of the combined devices under a load (W) applied from above.

The stiffening ability of the stiffening portion when inserted into the distal end of the lumen opening of feeding tube 20 was tested. An illustration of the testing set-up is shown in FIG. 6. In the test there were two supporting points, S1 and S2 spaced "L" distance apart, in contact with the feeding tube 20: one support point near each of the proximal and distal ends of the stiffening portion 18. The feeding tube was a 24 French, 6 cm, MIC-KEY® Secure Flow gastrostomy tube commercially available from Kimberly-Clark Corporation, having an outside diameter of 8 mm and an inside diameter of about 5.5 to 6.5 mm. The dilation device 10 had an overall length of about 8 cm and a stiffening portion with an outside diameter of 7 mm and a length of 28 mm. The deflated stiffening portion 18 of the dilation device was placed within the interior lumen of the MIC-KEY® SF feeding tube and fully inflated to three pressure conditions of 0, 15 and 25 psi. Loads were applied to the tube, e.g. on top at the midpoint, L/2, between the supports (L was 25 mm). A baseline load state was defined when the stiffening portion 18 was at 0 psi (0 bar) and slight deflection was observed to occur at a load W of 0.8 pounds (0.36 kg). Two additional load states were measured at 15 psi (1.03 bar) and 25 psi (1.72 bar) inflation pressure in the non-compliant stiffening portion when the observed deflection was less than the baseline state. The loads W sustained prior to observed deflection at these pressures were 1.2 lbs. (0.55 kg) and 1.5 lbs. (0.68 kg), respectively. This test shows that the inserted and pressurized device into the feeding tube makes the feeding tube less likely to bend or kink so that, by inference, they would be easier to push into position in the stoma compared to the feeding tube alone.

Figure 7:
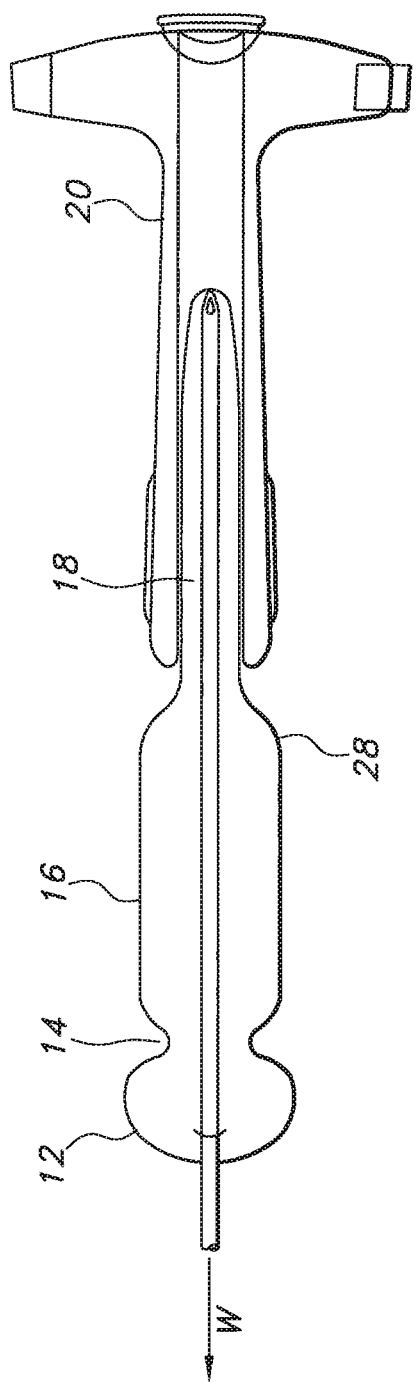
FIG. 7 shows a device with the stiffening portion inserted into a feeding tube with a load (W) applied in the distal direction to determine the gripping force of the stiffening portion within the feeding tube.

A further test was performed to directly measure the gripping ability of the stiffening portion 18 in a feeding tube 20. An illustration of the testing set-up is shown in FIG. 7. The same dilation device and feeding tube as above were used. The deflated stiffening portion 18 of the dilation device was placed in the interior lumen of the MIC-KEY® SF feeding tube and inflated to two pressure conditions. The stiffening portion 18 was non-compliant so its outside diameter must necessarily be slightly larger than the inside diameter of the lumen of feeding tube catheter 20. The proximal end of the MIC-KEY® SF device was fixed and a load W was applied in the distal direction to the dilation device at its distal end along the longitudinal axis of the combined device and feeding tube. At full inflation but at a pressure of 0 psi there is no holding force when the dilation device is pulled away from the feeding tube so it separates easily from the feeding tube. When the stiffening portion 18 was inflated to 15 psi its diameter compressed against the inside lumen of the feeding tube 20, creating friction between the dilation device and the feeding tube. A pulling force of 6.5 lbs (28.9 Newtons) in the direction along the longitudinal axis of the device and feeding tube was achieved without separation when an attempt to separate the devices was made at the 15 psi inflation pressure. This holding force can be used to allow the tube to be pulled into place, assisting in placement and making it likely that the surgeon will assist by pushing the feeding tube in conjunction with the pulling force from the dilation device. It is believed therefore that a pressure in the stiffening portion of at least 15 psi can provide sufficient friction between the stiffening portion and a feeding tube to allow for easier placement of the dilation device. In any event a pressure greater than 0 psi should be used to maintain the stiffening section of the device and the feeding tube in contact.

The dilation device 10 may be formed of materials such that the retention portion 12 and dilation and stiffening portions 16 and 18 are compliant, semi-compliant, or non-compliant, or have combinations of such compliances, though the stiffening portion 18 is desirably non-compliant. That is, the portions may exhibit parts that are relatively elastomeric (e.g., compliant) so that these parts stretch as well as expand upon inflation. The portions may also exhibit parts that are somewhat elastomeric (e.g., semi-compliant) so that they expand but have limited stretch upon inflation. The portions may exhibit parts that are non-elastomeric (e.g., non-compliant) so that they inflate without significant stretching of the material from which they are formed. The balloon may be formed of polyurethane material identified as Pellethane® 2363-90A, available from Lubrizol Advanced Materials, Inc., Thermedics™ Polymer Products.

Inside-Out Placement

According to this disclosure, the dilation device may be utilized in an "inside-out" dilation procedure. Inside-out dilation involves attachment of the dilation device to the guide wire outside of the patient's mouth or inside the non-vascular lumen (e.g., the stomach or other space). An example of attachment outside the patient's mouth may involve the following steps: insertion of an endoscope into the mouth and to the stomach; conventional placement of a guide wire through the skin, abdominal wall and stomach wall utilizing a needle; insertion of a standard endoscopic forceps or an endoscopic snare through the working channel of the endoscope; using the forceps or snare to grasp the guide wire in the stomach and then pulling the guide wire through the working channel of the endoscope and out of the patient's mouth (unlike current practice where the entire endoscope is removed from the patient); securely attaching the end of the dilation device closest the stiffening portion 18 (the proximal end, e.g. via Loop 30) to the end of the guide wire that extends from the patient's mouth; pulling the guide wire and attached dilation device back through the working channel of the endoscope via the guide wire that remains outside the skin so that the dilation device exits the working channel, into the stomach, and partially through the stomach wall, abdominal wall and skin so that the stiffening portion protrudes away from the skin.

Another example of attachment of the dilation device to the guide wire is inside the patient's stomach and may involve the following features and/or steps: the dilation device contains a fixture (magnet, hook, loop, snare, etc.) at the end of the device that enters the mouth first; the dilation device is pushed through the working channel of the endoscope so that the fixture exits the working channel into the stomach; the fixture is attached under visualization of the endoscope by connecting the fixture to the guide wire (that was inserted into the stomach via through a needle).

The inside-out placement of the dilation device involves the following steps:

An endoscope (not shown) may be advanced into a non-vascular lumen (e.g., the stomach) to insufflate and allow palpation to locate a catheter tube location site (e.g., a PEG location site). The endoscope is typically advanced through the mouth and throat (esophagus) of the patient to the stomach. Once the site is located, a needle may be inserted from outside the body, through the skin and abdomen and into the stomach. A guide wire is then introduced into the stomach through the needle tract. The needle may be removed from the stomach, while retaining the guide wire in the needle tract.

Standard endoscopic forceps, an endoscopic snare, or a balloon attachment fixture may be inserted through the working channel of the endoscope into the stomach. The forceps, snare or fixture is used to grasp the guide wire 22 and the guide wire 22 is pulled up through the working channel of the endoscope and out of the patient's mouth.

A dilation device with its attached inflation lumen is secured to the end of the guide wire and is pulled through the working channel of the endoscope using the guide wire and into the stomach. The dilation device has a diameter that fits within the working channel of the endoscope. Typically, the diameter is in the range of about 2 millimeters or less. The dilation device is pulled up into and partially through the needle tract so that it reaches the abdominal tissue and the skin on the exterior 50 of the patient.

Outside-In Placement

According to this disclosure, the dilation device may also be utilized in "outside-in" dilation procedures. One outside-in dilation procedure involves initial positioning of the dilation device over the guide wire outside of the patient's stomach. This procedure requires that the device 10 to have a continuous pathway through its center so that it may be mounted on a guide wire. Conventional placement of a guide wire through the skin, abdominal wall and stomach wall is achieved utilizing a needle.

Dilation device 10 inserts over the guide wire so that the dilation portion 16 (and any retention portion 12) furthest away from the stiffening portion 18 enters the stomach. This placement may be achieved by direct insertion of the dilation device through the needle tract formed by insertion of the needle. Alternatively, an introducer, e.g. cannula, inserts into the needle tract over the guide wire and to the stomach to provide a conduit for the device; the device fits within the introducer and once the device is properly positioned (as previously describe) the introducer is removed. The introducer can be a splittable cannula or sleeve.

Figure 5:
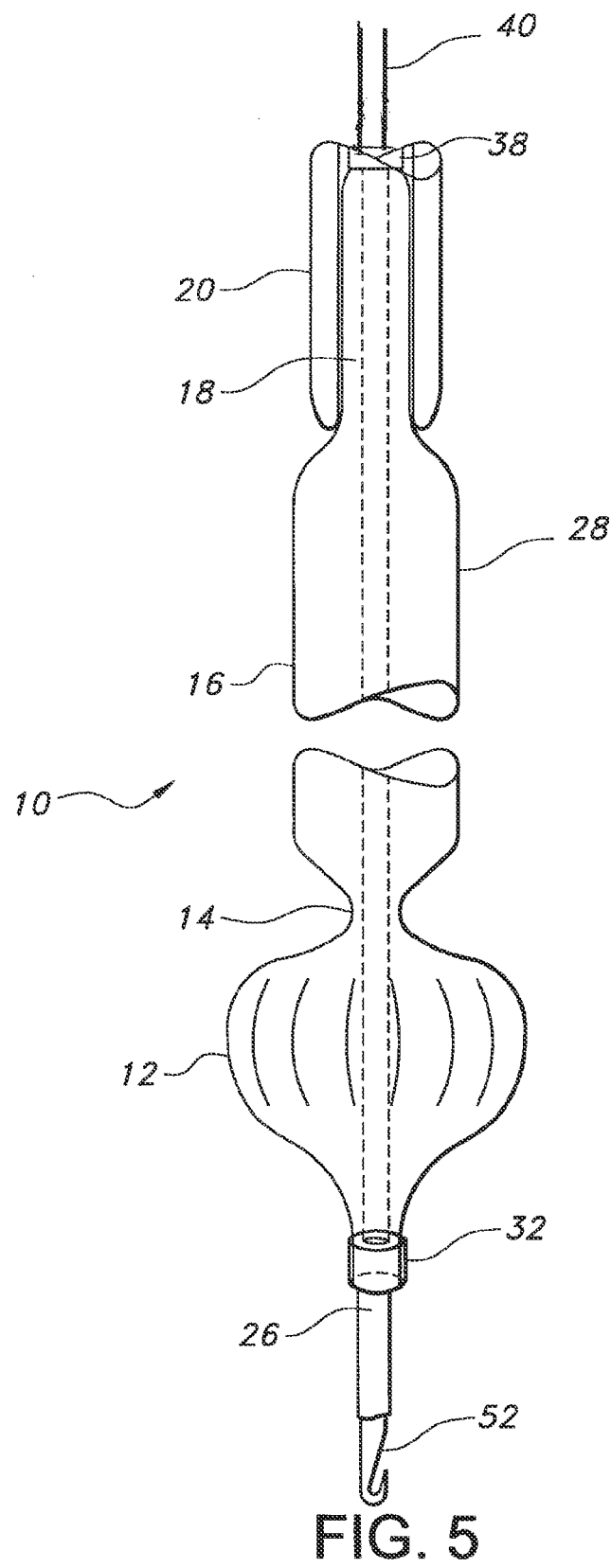
FIG. 5 shows a device with a distal end having a hook that may be used to pull the device from outside the body into the body for the outside-in installation.

FIG. 5 shows a device 10 with a hook 52 located on the distal end that would be suitable for outside-in placement. The hook 52 may be similar in shape to a crochet needle hook and should be sufficient for a loop of line or other means of attaching to grip the hook 52. The outside-in device has its inflation lumen 40 on the proximal end of the device 10, opposite the configuration in FIGS. 1, 2 and 3 and so has no pull loop 30. The device 10 may be, in all other aspects similar to the embodiments of FIGS. 1, 2 and 3, that is, it may contain a single balloon or multiple balloons that may be inflated separately and be attached to the tubular support 26 at collars 32, 38. In use the hook 52 and tubular suppost 26 are advanced into the needle tract from outside of the patient and the hook 52 is grabbed by the snare of the endoscope. The endoscope is then used to pull the device into the patient to the desired position. Once the device is properly positioned, dilation is the same as with an inside-out installation. After use the device may be withdrawn through a channel of the endoscope or withdrawn with the endoscope as it is withdrawn.

Regardless of the steps used to place the dilation device in the stomach, after placement in the stomach the device is pulled into and partially through the needle tract or stoma so that the stiffening portion 18 and at least a part of the deflated dilation portion 16 extends through the abdominal tissue and the skin, and any retention portion 12 resides in the stomach.

For positioning the dilation device 10 in the stoma, the inflatable components, e.g. balloon 28, must be deflated so that the dilation device 10 easily slides through the working channel of the endoscope and/or it penetrates the needle tract without excessive force. In this deflated state the components desirably wrap and fold around the tubular support 26 as much as possible to minimize the effective cross-sectional area of the dilation device 10 during insertion through the endoscope and/or needle tract. Such folding and wrapping is achieved by intentionally folding balloon walls in pre-planned arrangements, via the use of a pleater and/or folder manufacturing apparatus, by random overlapping and folding afforded by the flexible nature and thinness of the balloon walls, or by such combinations.

When it is desired to remove the device 10 from the patient, the inflated components may be deflated. Once deflated, the device is either pulled back through the endoscope's working channel by the end with the inflation lumen, it is pulled out together with removal of the endoscope from the patient, or it is removed through the (central) channel of the feeding tube. Whichever method of placement and withdrawal is chosen, it is clear that the endoscope inserts into the non-vascular lumen only once, reducing the time of the placement and reducing the trauma experienced by the patient.

This disclosure also includes a system for dilating a stoma and inserting a non-vascular catheter tube, the system includes a stoma dilation device as described above. The system also includes a non-vascular catheter feeding tube configured to fit over the fully or partially inflated stiffening portion of the device prior to insertion of the catheter tube through the dilated stoma tract and into the area of the non-vascular lumen.

According to an aspect of this disclosure, the fully inflated diameter of the dilation portion 16 may be selected from a range to match the diameter of the catheter tube 20 (e.g., the PEG device) that will be inserted. The dilation portion 16 may have at least one diameter(s) and the retention portion 12 may have at least one diameter that is greater than the dilation portion 16.

According to an aspect of this disclosure, after the dilation device has its inflatable portions inflated to the desired pressures and the stiffening portion 18 is firmly joined to the tube 20, the device 10 may be advanced into the stoma. The pressure of the dilation portion 16 may be reduced slightly if desired to allow the dilation portion 16 to more easily slide into the stomach.

According to an aspect of this disclosure, the feeding tube 20 may be placed in the stoma by either a "push" method or a "pull" method. In the push method, the device 10 is advanced into the stomach by pushing the tube 20 into the stoma. The feeding tube 20 should be held as closely as possible to the patient's body and gently but firmly advanced into the stoma. In the pull method, the device is advanced by gently pulling the device 10 in the direction of the endoscope or simply by slowly retracting the endoscope from the patient. The feeding tube 20, firmly attached to the device 10 by the gripping of the stiffening portion 18 within the tube 20, will be drawn into the stoma by the retraction of the device 10. Whether placed by the "push" or "pull" method, the distal end of the catheter feeding tube 20 becomes positioned in the stoma. The retention device of the feeding tube 20 should now be deployed to hold the tube 20 in position and to hold the gastric lumen against the abdominal wall, as is known in the art. At this point, the inflated portions may be fully deflated and the device 10 withdrawn completely from the patient. The dilation device 10 with its inflatable components completely deflated, may be removed through the working channel of the endoscope. Alternatively, the device 10 may be removed with the endoscope by retracting or withdrawing the endoscope from the patient, rather than through the endoscope. In still another alternative, the device 10 may be removed through the lumen of the feeding tube 20 provided of course that it is sized to fit through the tube 20.

While this disclosure has been described in connection with certain preferred embodiments it is to be understood that the subject matter encompassed by way of this disclosure is not to be limited to those specific embodiments. On the contrary, it is intended for the subject matter of this disclosure to include all alternatives, modifications and equivalents as can be included within the spirit and scope of the following claims.

What is claimed is:

1. A dilation device comprising: a tubular support comprising a proximal end and distal end; a balloon comprising a retention portion configured with the proximal end of the tubular support, an inflatable dilation portion proximal the retention portion, an inflatable stiffening portion proximal the inflatable dilation portion, and a flexible portion connecting the retention portion and the inflatable dilation portion, the retention portion comprising a larger cross-section than the inflatable dilation portion when inflated, the flexible portion having a smaller cross-section than the retention portion and the inflatable dilation portion; a catheter tube fitted over the stiffening portion, the stiffening portion abutting against an inside surface of the catheter tube via friction after the stiffening portion is inflated; and an inflation lumen configured through the balloon.

2. The device of claim 1, wherein the balloon is constructed from at least one of compliant material, a non-compliant material, or a semi-compliant material and combinations thereof.

3. The device of claim 1, wherein the inflatable dilation portion and the retention portion are constructed from different materials.

4. The device of claim 1, wherein said catheter tube is configured to be pushed into a non-vascular lumen while attached to said stiffening portion of said device by friction.

5. The device of claim 1, wherein said catheter tube is configured to be pulled into a non-vascular lumen while attached to said stiffening portion of said device by friction.

6. The device of claim 1, wherein said stiffening portion is inflated to at least 15 psi prior to placement of said device.

7. The device of claim 1, further comprising a continuous pathway through the device.

8. The device of claim 1, further comprising a first collar configured with the retention portion at the proximal end of the tubular support.

* * * * *